United States Patent [19]

Chung

[11] Patent Number: 4,460,691

[45] Date of Patent: Jul. 17, 1984

[54] STREPTOMYCES PLASMID PROPHAGE PUC13

[75] Inventor: Shiau-Ta Chung, Portage, Mich.

[73] Assignee: The Upjohn Company, Kalamazoo, Mich.

[21] Appl. No.: 291,726

[22] Filed: Aug. 10, 1981

Related U.S. Application Data

[63] Continuation-in-part of Ser. No. 278,784, Jun. 29, 1981, abandoned.

[51] Int. Cl.³ .................. C12N 1/20; C12N 1/00; C12R 1/54; C12N 7/00; C12P 21/00; C12N 15/00; C12N 7/02
[52] U.S. Cl. .................. 435/235; 435/253; 435/317; 435/896; 435/68; 435/172.3; 435/239; 935/28; 935/29; 935/31; 935/69; 935/73; 935/74; 935/75
[58] Field of Search .................. 435/68, 70, 172, 253, 435/317, 896, 235, 239

[56] References Cited

FOREIGN PATENT DOCUMENTS 8007080 10/1980 United Kingdom .

OTHER PUBLICATIONS

Fredrickson, D. S. 1980, "Guidelines for Research Involving Recombinant DNA Molecules" Fed. Reg. 45, 6724–6749.

Bibb, M., et al. 1980, A DNA Cloning System for Interspecies Gene Transfer in Antibiotic-Producing Streptomyces, Nature 284, 526–531.

Suarez, J. E. et al. 1980 DNA Cloning in Streptomyces: a Bifunctional Replicon . . . Nature 286, 527–529.

Schottel, J. L. et al. 1981. Cloning and Expression of Streptomyces lividans . . . J. Bacteriol. 146, 360–368.

Suarez et al, J. Bacteriol. 142, 8 (1980).

Komatsu et al, in Microbiology, (1981) D. Schlessinger (ed.), pp. 384–387, ASM Publications, Washington, D.C.

Okanishi, in Molecular Breeding and Genetics of Applied Microorganisms, Sakaguchi et al (ed.), Academic Press, New York, 1980, p. 43.

Primary Examiner—Thomas G. Wiseman
Assistant Examiner—James Martinell

[57] ABSTRACT

A novel plasmid cloning vector, designated pUC13, can be used, advantageously, in recombinant DNA work. This plasmid has been identified as a prophage. The procedures used to recognize this prophage can be used to recognize other prophages in Streptomyces.

10 Claims, No Drawings

STREPTOMYCES PLASMID PROPHAGE PUC13

CROSS REFERENCE TO RELATED APPLICATION

This is a continuation-in-part of my pending application Ser. No. 278,784, filed on June 29, 1981 now abandoned.

BACKGROUND OF THE INVENTION

The application of recombinant DNA technology to industrial microbiology and genetics is rapidly developing. Part and parcel of recombinant DNA technology is the insertion of foreign DNA into a vector which will allow the introduction and maintenance of this DNA in a useful host. Such host-vector systems have been described for the organisms *Escherichia coli, Bacillus subtilis, Neurospora crassa* and *Saccharomyces cerevisiae*. [Fredrickson, D. S. 1980. "Guidelines for research involving recombinant DNA molecules". Fed. Reg. 45, 6724–6749]. A number of vectors, both phage and plasmid, have been developed for use in these systems. Recent scientific and patent literature describes two similar systems in species of the genus Streptomyces. [Bibb, M., Schottel, J. L., and Cohen, S. N. 1980. A DNA cloning system for interspecies gene transfer in antibiotic-producing Streptomyces. Nature 284, 526–531. Suarez, J. E., and Chater, K. F. 1980. DNA cloning in Streptomyces: a bifunctional replicon comprising pBR322 inserted into a Streptomyces phage. Nature 286, 527–529. Schottel, J. L., Bibb, M. J., and Cohen, N. C. 1981. Cloning and expression in Streptomyces lividans of antibiotic resistance genes derived from *Escherichia coli*. J. Bacteriol. 146, 360–368.]

Plasmid pUC1 is obtainable from a biologically pure culture of the microorganism *Streptomyces fradiae*, NRRL 11443. This plasmid is disclosed in British patent application No. 8007080 which was published on Oct. 29, 1980, with the publication No. 2,045,253.

BRIEF SUMMARY OF THE INVENTION

Plasmid pUC13 is obtainable from the microorganism *Streptomyces fadiae*, NRRL 12494. This plasmid can be obtained from NRRL 12494 by growing the culture on a suitable medium, fragmenting the mycelia, incubating the fragmented mycelia, harvesting the culture after a suitable time, and then lysing the mycelia. From this lysate it is possible to isolate essentially pure pUC13. Plasmid pUC13 sensitivities to a variety of restriction endonucleases allows for its ready modication and adaptation to a number of host vector systems.

Plasmid pUC13 is a prophage state of an actinophage, designated herein as $\phi$SFl, of *S. fradiae*. Thus, pUC13 DNA from *S. fradiae* can be used to transfect protoplasts of plasmid cured Streptomyces and Micromonospora hosts.

Though plasmid pUC13 is related to plasmid pUC1, it is distinctly different in several key areas. pUC13 is different from pUC1 in that it is a high copy number variant (3–5×) of pUC1. The restriction enzyme cleavage pattern and molecular weight of pUC13 are identical to that of pUC1. pUC13 can be transformed into plasmid cured cultures and give plaques on the transformation plates, while pUC1 gives pocks on the transformation plates when transformed in the same manner. Therefore, pUC13 is a genetic variant of pUC1.

DNA of $\phi$SFl phage obtained from the strain containing pUC13 exists as a linear form, and has a molecular weight of $55.7 \pm 1.8 \times 10^6$ which is about 10% larger than pUC13 DNA. Since the restriction enzyme cleavage pattern of $\phi$SFl DNA is identical to that of pUC13, $\phi$SFl lysogen of plasmid cured *S. fradiae* strain contains pUC13 plasmid, and transformation of plasmid cured *S. fradiae* protoplasts with pUC13 DNA yields $\phi$SFl, it is concluded that pUC13 plasmid is a prophage state of $\phi$SFl.

$\phi$SFl has a polyhedral head and a long tail with a terminal structure. Measurements taken from 20 particles are as follows: head length $93.7 \pm 4.5$ nm; head width $86.9 \pm 3.2$ nm; tail length $257.8 \pm 5.2$ nm; tail width between 8 to 10 nm.

$\phi$SFl possess the following novel properties:
A. Ability to transduce auxotrophic markers;
B. Ability to be maintained in its host as a plasmid and be transferred readily from host to host in the form of a bacteriophage;
C. pUC13 DNA, a prophage state of $\phi$SFl, can be transformed into plasmid cured strain and recognized by the expression of plaque formation; and,
D. $\phi$SFl is infectious to

*Streptomyces lincolnensis, Streptomyces espinosus* and *Streptomyces coelicolor*.

$\phi$SFl and its prophage, pUC13, are very valuable cloning vectors and genetic mapping tools for Streptomyces and Micromonospora.

DETAILED DESCRIPTION OF THE INVENTION

The Microorganism pUC13 is obtainable from *Streptomyces fradiae* NRRL 12494. This biologically pure culture is available from the permanent collection of the Northern Regional Research Laboratory, U.S. Department of Agriculture, Peoria, Ill., U.S.A.

Characteristics of pUC13

Molecular Weight: ca. $50.41 \pm 2.6$ megadaltons.
Copies Per Cell: 3–5.
Restriction Endonuclease Sensitivities:
pUC13 has the following sensitivies to restriction endonucleases.

Plasmid Sensitivities To Restriction Endonucleases

| Enzyme | # Cleavage Sites pUC13 | Enzyme | # Cleavage Sites pUC13 |
|---|---|---|---|
| BamH I | $\geq 15$ | Hind III | 2 |
| EcoR I | 0 | Kpn I | $\geq 15$ |
| Pst I | $\geq 18$ | Xho I | $\geq 15$ |
| Xba I | 2 | Sma I | $\geq 15$ |
| Bgl II | 5 | Bcl I | 7 |

These results are obtained by digestion of pUC13 DNA in the presence of an excess of restriction endonuclease. The number of restriction sites are determined from the number of resolvable fragments in either 0.7 or 1.0% agarose gels.

*Streptomyces fradiae*, NRRL 12494 can be grown in an aqueous nutrient medium under submerged aerobic conditions. The organism can be grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, manganese, cobalt, iron, and the like, need not be added since tap water and unpurified ingredients are used as components of the medium prior to sterilization of the medium.

The inoculated medium can be incubated at any temperature conducive to satisfactory growth of the microorganism, for example, between about 18° and 50° C., and preferably between about 20° and 37° C. Ordinarily, optimum growth of the microorganism is obtained in about 3 to 15 days. The medium normally remains acidic during the growth cycle. The final pH is dependent, in part, on the buffers present, if any, and in part on the initial pH of the culture medium.

The following examples are illustrative of the process and products of the subject invention but are not to be construed as limiting. All percentages are by weight and all solvent mixture proportions are by volume unless otherwise noted.

EXAMPLE 1

Isolation of Plasmid pUC13 from a Biologically Pure Culture of Streptomyces fradiae, NRRL 12494

The spores from a biologically pure culture of *Streptomyces fradiae*, NRRL 12494 are inoculated into 10 ml of the following medium which contains 1% glucose; 0.4% peptone; 0.4% yeast extract; 0.05% $MgSO_4.7H_2O$; 0.2% $KH_2PO_4$; and 0.4% $K_2HPO_4$.

The medium has previously been sterilized in 50 ml Erlenmeyer flask. After inoculation, the flask is incubated at 32° C. for about 24 to 36 hours on a Gump or New Brunswick rotary shaker operating at 100–250 rpm. Upon completion of the incubation, 0.5 ml of the culture is transferred into 10 ml of the above medium containing 0.5 to 2.0% (w/v) glycine in a 50 ml Erlenmeyer flask. The addition of glycine facilitates the subsequent lysing of the cells. The amount of glycine in the medium can be varied by routine adjustments with the goal being to facilitate the subsequent lysing of the cells. The flask is then incubated further for another 24 to 36 hours at 32° C. on a Gump rotary shaker, as above. After this incubation, the mycelia are separated from the broth by low speed centrifugation, for example, at $6000 \times g$ for 15 minutes at 4° C. and decantation of the supernatant from the mycelial pellet.

The supernatant is discarded and the pellet is resuspended in 1.5 ml of an isotonic buffer, e.g. TES buffer [0.03 M tris(hydroxymethyl)-aminomethane (Tris), 0.005 M EDTA and 0.05 M NaCl; pH=8.0] containing 20% (w/v) sucrose. Next, 0.3 ml of a 5 mg/ml lysozyme and 0.15 ml of a 1 mg/ml RNase in the same buffer are added and the mixture is incubated at 37° C. for 30 minutes with occasional mixing. Then, 0.6 ml of 0.25 M EDTA (pH=8.0) is added and this mixture is incubated 15 minutes at 37° C. Then 0.3 ml of 5 mg/ml pronase is added and the material is incubated 10 minutes at 37° C. Subsequently, the cell suspension is lysed by the addition of 3.0 ml of a 2% sarkosyl in TES buffer and incubation of this mixture at 37° C. for 20–30 minutes. The lysate is then sheared by passing it 5–10 times through a 50 ml disposable syringe without a needle.

This crude lysate material is then mixed with a salt, for example, cesium chloride (preferred), or cesium sulfate, and the intercalating dye ethidium bromide to give a solution of density = 1.550. This solution is centrifuged to equilibrium at $145,000 \times g$ (isopycnic density gradient centrifugation). The covalently closed circular plasmid DNA is then visible in the centrifuge tube under long wave ultraviolet (320 nm) illumination as a faint fluorescent band below the intensely fluorescent band of linear chromosomal and plasmid DNAs.

Covalently closed circular plasmid DNA is prepared for characterization by removing it from the isopycnic gradients, extracting the ethidium bromide by two treatments with one third volume of isopropyl alcohol and then dialyzing the aqueous phase against an appropriate buffer, e.g. $0.1 \times SCC$ buffer (0.015 M NaCl, 0.0015 M $Na_3C_6H_5O_7.2H_2O$; pH=7.4) to yield essentially pure pUC13.

Procedures For Characterizing pUC13

An estimate of pUC13 molecular weight is obtained by electron microscopy of individual DNA molecules [Kleinschmidt, A. K. (1968). Monolayer techniques in electron microscopy of nucleic acid molecules. In "Method of Enzymology" (S. P. Colowick and N. O. Kaplan, eds.) Vol. 12B, pages 361–377. Academic Press, New York]. Plasmid pUC13 is found to have an average contour length of $25.72 \pm 1.32$ μm and a corresponding molecular weight of $50.41 \pm 2.60$ megadaltons when using plasmid pML31 having a molecular weight of $10.32 \times 10^6$ as an internal control.

The percent plasmid DNA in *Streptomyces fradiae* NRRL 12494 is determined by labeling the culture with [methyl-$^3$H]thymidine, preparing crude lysates, and centrifuging samples of the lysates in cesium chloride ethidium bromide density gradients. The gradients are fractionated, the isotopic counting performed, and the percent radioactivity in the plasmid band used to quantitate the plasmid DNA and calculate the plasmid copy number [Radloff, R., Bauer, W. and Vinograd, J. 1967. "A dye-buoyant density method for detection and isolation of closed circular duplex DNA: The closed circular DNA of HeLa cells". Proc. Nat. Acad. Sci. USA 57, 1514–1520].

Restriction Endonuclease Digestion And Agarose Gel Electrophoresis

Restriction endonucleases can be obtained as commercial preparations from Miles Laboratories, BRL, and New England Biolabs. Enzyme digestions are prepared in accordance with the conditions specified by the suppliers using at least a two-fold excess of endonuclease.

In some tests plasmid DNA is digested with more than one endonuclease. Two methods are used in these tests. In the first method, the plasmid DNA is digested first with the enzyme having the lower ionic strength requirements, and then digested with the enzyme having higher ionic strength requirements after the addition of an equal volume of $2\times$ buffer of the second enzyme. In the second method, restriction fragments of one enzyme digest are isolated from a preparative agarose gel as described by Tanaka and Weisblum [Tanaka, T., and Weisblum, B. 1975. Construction of a colicin E1-R factor composite plasmid in vitro: Means for amplification of deoxyribonucleic acid. J. Bacteriol. 121, 354–362].

The isolated restriction fragments are concentrated by ethanol precipitation and then digested with other restriction enzymes. Double digest experiments are compared with single digest experiments to ensure that no abnormal restriction patterns are obtained, i.e. no non-specific cleavage of DNA by an enzyme occurs after altering the ionic strength of the digestion mixture.

The digested samples are applied to 0.7-1% agarose gels and are electrophoresed for 2 hours at a constant applied voltage of 10-15 v/cm of gel height. [Sharp, P. A., Sugden, J. and Sambrook, J. 1973. Detection of two restriction endonuclease activities in *Haemophilus parainfluenzae* using analytical agarose-ethidium bromide electrophoresis. Biochemistry 12, 3055-3063]. The molecular weights of restriction fragments are determined relative to the standard migration patterns of bacteriophage lambda DNA digested with enzyme EcoRI [Helling, R. B., Goodman, H. M. and Boyer, H. W. 1974. Analysis of endonuclease R.EcoRI fragments of DNA from lambdoid bacteriophages and other viruses by agarose-gel electrophoresis. J. Virology 14, 1235-1244].

EXAMPLE 2

Process To Obtain Actinophage Designated φSF1

Plasmid prophage DNA, pUC13, obtained as described in Example 1, is used to transfect protoplasts of a plasmid cured Streptomyces host. "Plasmid cured", as the term is used herein, means a host which does not have a plamid, or if a plasmid is present, it does not interfere with transfection. A standard process to cure a host, for example, *S. fradiae* containing plasmid pUC1, is to grow this microorganism in S-medium [Okanishi, M. Suzuki, K. and Umezawa, H. 1974. formation and reversion of Streptomycete protoplasts: cultural condition and morphological study. J. Gen. Microbiol. 80, 389-400.] containing 2 mg./ml. of novobiocin at 32° C. for two to three days. The cultures are then plated out to obtain single plasmid cured colonies.

Protoplasts for transfection can be prepared from vegetative mycelia in the following manner. Spores are inoculated into S-medium and grown 24-48 hrs at 32° C. This culture is homogenized and used to inoculate fresh S-medium cultures containing 1.0% glycine. The glycine supplemented cultures are grown another 24-48 hrs. at 32° C., harvested by centrifugation at 3000×g, washed once with 0.3 M sucrose and resuspended in 0.3 M sucrose. This suspension is sonicated 25-30 min. in a Bronson model 220 ultrasonic water bath, pelleted at 3000×g and the pellet is resuspended in P-medium [Okanishi, M., Suzuki, K. and Umezawa, H. 1974. Formation and reversion of streptomycete protoplasts: cultural condition and morphological study. J. Gen. Microbiol. 80, 389-400.] containing 5 mg/ml lysozyme. The mycelia and lysozyme are incubated at 37° C. until protoplasts are released. Mycelial debris are removed from the protoplast suspension by filtration through a sterile cotton plug. Residual lysozyme is removed by twice pelleting the protoplasts and washing them with P-medium. Finally, protoplasts are resuspended in P-medium.

Protoplast transfection can be done in the following manner. Approximately $2 \times 10^7$ protoplasts are pelleted by centrifugation at 1,000 g for 7 minutes. The supernatant is removed and the protoplasts are gently resuspended in a minimum volume of buffer remaining with the pellet. To each aliquot of protoplasts, 20 μl of sterile TE buffer (10 mM Tris.HCl, 1 mM EDTA, pH 8.0) containing varying amount of pUC13 DNA are added with gentle mixing. 0.5 ml of varying concentrations of polyethylene glycol 1000 in P-medium are added, followed 1 minute later by an equal volume of a pEG 1000 solution at half the original concentration and, after a further 3 minutes, 4 ml of P-medium. The suspensions are resuspended in 0.3 ml of P-medium. 0.1 ml of the suspensions are overlaid along with $2 \times 10^7$ spores of plasmid cured strain on R2 medium [Okanishi, M., Suzuki, K. and Umezawa, H. 1974, supra] containing 1% glucose and 1% yeast extract. The plates are incubated at 32° C.

EXAMPLE 3

Other Streptomyces prophages can be detected by transformation of protoplast of a plasmid cured strain, using the procedures disclosed in Example 2, with other Streptomyces plasmid DNA. The presence of plaques on the transformation plates indicates that the plasmid is a prophage.

EXAMPLE 4

Recombinant and genetically marked actinophage can be obtained by transfection of a recombinant plasmid prophage DNA in Streptomyces species by substituting said recombinant plasmid prophage DNA for plasmid prophage DNA in Example 2. Illustrative of this process is the cutting of pUC13 into $49.5 \times 10^6$ and $0.5 \times 10^6$ dalton pieces by endonuclease HindIII. The small fragment, which is determined to be non-essential to infection activity, can be deleted to give a recombinant plasmid, which can be used as a vector for cloning DNA in a suitable host microbe, e.g. a prokaryote or lower eukaryote. For example, foreign DNA, such as a glucose isomerase gene, can be cloned into the single Hind III site of this derivative of pUC13. In a similar manner, other actinomycete prophages which exist as autonomously replicating plasmids like pUC13 can be used as vectors in host-vector systems.

EXAMPLE 5

By substituting plasmid prophage pUC13 in Example 2 with other Streptomyces plasmic prophage DNA, actinophage is obtained. Actinophages can be recognized in a plasmid cured host population at a frequency of $\leq 10^{-9}$ by the phenotype of "lethal zyogsis" or plaque formation.

EXAMPLE 6

A Process To Isolate And Develop Strains Containing Plasmid Prophages In Streptomyces From Soil Samples This process includes the following procedures:
(1) Non-lysogenic strains of Streptomyces are grown with various soil samples in a rich medium, such as S-media, for two to three days. After membrane filtration of the cultures, the filtrate is diluted and examined for the phage plaque forming activity with spores of plasmid cured strains;
(2) lysogenic strains are isolated from centers of plaques, purified and tested for the ability to cause the lethal zyogsis or plaque phenotype against non-lysogenic strains; and,
(3) strains which cause the lethal zyogsis or plaques are tested for the presence of plasmid.

The work described herein was all done in conformity with physical and biological containment requirements specified in NIH Guidelines.

I claim:

1. Biologically pure *Streptomyces fradiae* (pUC13) having the deposit accession number NRRL 12494.

2. Biologically pure plasmid prophage pUC13, which has the following characteristics:
   (a) molecular weight of 50.4±2.6 megadaltons
   (b) 3–5 copies per cell;
   (c) sensitivities to restriction endonucleases as follows:

| Enzyme | pUC13 | Enzyme  | pUC13 |
| ------ | ----- | ------- | ----- |
| BamH 1 | ≧15   | Hind III | 2    |
| EcoR 1 | 0     | Kpn I   | ≧15   |
| Pst I  | ≧18   | Xho I   | ≧15   |
| Xba I  | 2     | Sma I   | ≧15   |
| Bgl II | 5     | Bcl I   | 7     | and,
   (d) when transformed into plasmid cured Streptomyces cultures gives plaques on the transformation plates.

3. Biologically pure actinophage obtained from pUC13 designated φSF1, which has the following characteristics:
   (a) linear form;
   (b) molecular weight of $55.7 \pm 1.8 \times 10^6$;
   (c) restriction enzyme cleavage pattern identical to that of pUC13;
   (d) has a polyhedral head and a long tail with a terminal structure which measure as follows:
   head length—93.7±4.5 nm;
   head width—86.9±3.2 nm;
   tail length—257.8±5.2 nm;
   tail width—8 to 10 nm;
   (e) the ability to transduce auxotrophic markers; and,
   (f) the ability to be maintained in its host as a plasmid and be transferred readily from host to host as a bacteriophage.

4. A process for preparing actinophage which comprises transfecting protoplasts of plasmid cured *Streptomyces fradiae* hosts with plasmid prophage pUC13 DNA.

5. A process, according to claim 4, wherein said plasmid cured Streptomyces is *S. fradiae* and said plasmid prophage DNA is pUC13.

6. A process for preparing recombinant and genetically marked actinophage which comprises transfecting protoplasts of plasmid cured Streptomyces hosts with recombinant plasmid prophage pUC13 DNA.

7. A process, according to claim 6, wherein said recombinant plasmid prophage DNA is constructed by deletion of a $0.5 \times 10^6$ Hind III fragment from pUC13, and cloning foreign DNA into the remaining single Hind III site of the deletion mutant of pUC13.

8. Deletion mutant of pUC13 which is obtained by deletion of $0.5 \times 10^6$ Hind III fragment from pUC13.

9. A process for introducing DNA into a suitable host which comprises providing prophage pUC13, which exists as an autonomously replicating plasmid, as a vector and transfecting said host.

10. A process, according to claim 9, wherein said actinomycete prophage is pUC13.

* * * * *